United States Patent
Gastaldo

(10) Patent No.: US 10,082,425 B2
(45) Date of Patent: Sep. 25, 2018

(54) INTEGRATED CHROMATIC CONFOCAL SENSOR

(71) Applicant: UNITY SEMICONDUCTOR, Montbonnot-Saint-Martin (FR)

(72) Inventor: Philippe Gastaldo, Pontcharre (FR)

(73) Assignee: UNITY SEMICONDUCTOR, Montbonnot-Saint-Martin (FR)

( * ) Notice: Subject to any disclaimer, the term of this patent is extended or adjusted under 35 U.S.C. 154(b) by 0 days.

(21) Appl. No.: 15/282,305

(22) Filed: Sep. 30, 2016

(65) Prior Publication Data
US 2017/0276544 A1    Sep. 28, 2017

(30) Foreign Application Priority Data

Mar. 25, 2016 (EP) ..................................... 16305348
Jul. 20, 2016 (EP) ..................................... 16180407

(51) Int. Cl.
*G01J 3/02* (2006.01)
*G01J 3/453* (2006.01)
*G01J 3/18* (2006.01)

(52) U.S. Cl.
CPC ........... *G01J 3/0208* (2013.01); *G01J 3/0218* (2013.01); *G01J 3/18* (2013.01); *G01J 3/453* (2013.01)

(58) Field of Classification Search
CPC .. G01J 3/0208; G01J 3/18; G01J 3/453; G01J 3/0218; G01N 21/9501; G01N 21/9503; H01L 22/12; G02B 21/006; G02B 21/0064
See application file for complete search history.

(56) References Cited

U.S. PATENT DOCUMENTS

| 6,043,932 | A | 3/2000 | Kusunose |
| 6,639,681 | B1 * | 10/2003 | Magne ............... G01D 5/35383 |
| | | | 356/478 |
| 6,934,019 | B2 | 8/2005 | Geffen et al. |
| 2006/0115200 | A1 * | 6/2006 | Van Der Vliet ..... G02B 6/1228 |
| | | | 385/12 |
| 2012/0019821 | A1 * | 1/2012 | Chen .................. G02B 21/0032 |
| | | | 356/303 |

(Continued)

FOREIGN PATENT DOCUMENTS

FR    2950441 A1    3/2011
FR    3006758 A1    12/2014

OTHER PUBLICATIONS

Kim et al., "Chromatic confocal microscopy with a novel wavelength detection method using transmittance," Optics Express (2013), 21(5), pp. 6286-6294.

(Continued)

*Primary Examiner* — Dominic J Bologna
(74) *Attorney, Agent, or Firm* — Greer, Burns & Crain, Ltd.

(57) ABSTRACT

A confocal chromatic device is provided, including at least one chromatic lens with an extended axial chromatism; at least one broadband light source; at least one optical detector; and at least one measurement channel with a planar Y-junction made with a planar waveguide optics technology, and arranged for transferring light from the at least one light source towards the at least one chromatic lens and for transferring light reflected back through the at least one chromatic lens towards the at least one optical detector.

12 Claims, 3 Drawing Sheets

(56) References Cited

U.S. PATENT DOCUMENTS

| | | | |
|---|---|---|---|
| 2012/0057155 A1* | 3/2012 | Gastaldo | G02B 21/0016 356/237.5 |
| 2015/0219617 A1* | 8/2015 | Storz | G01N 27/24 356/72 |
| 2015/0260504 A1* | 9/2015 | Schonleber | G01B 9/02091 356/478 |
| 2016/0370172 A1* | 12/2016 | Christoph | G01B 5/012 |

OTHER PUBLICATIONS

European Search Report from European Patent Application No. 16305348.1, dated Jul. 6, 2016.

* cited by examiner

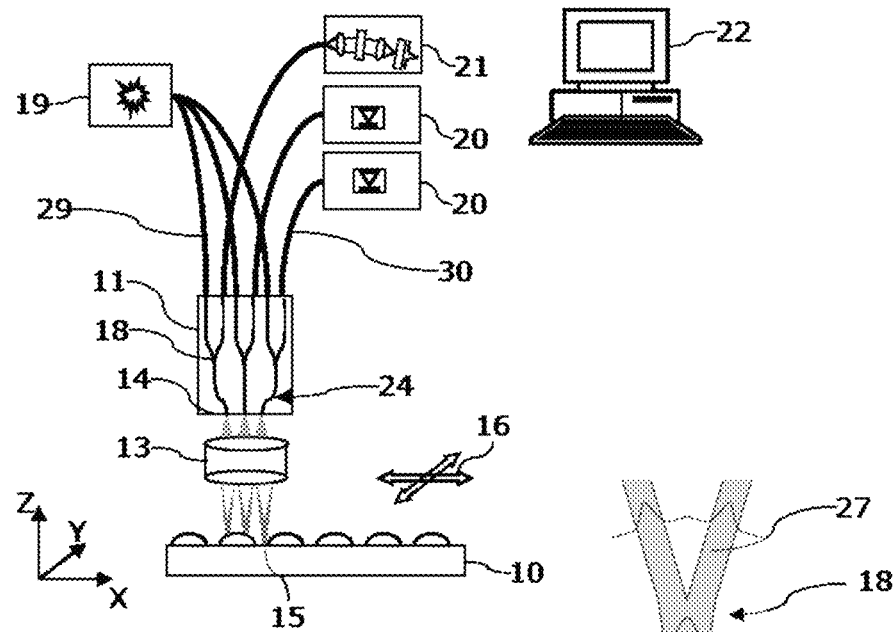
Fig. 1
Fig. 2
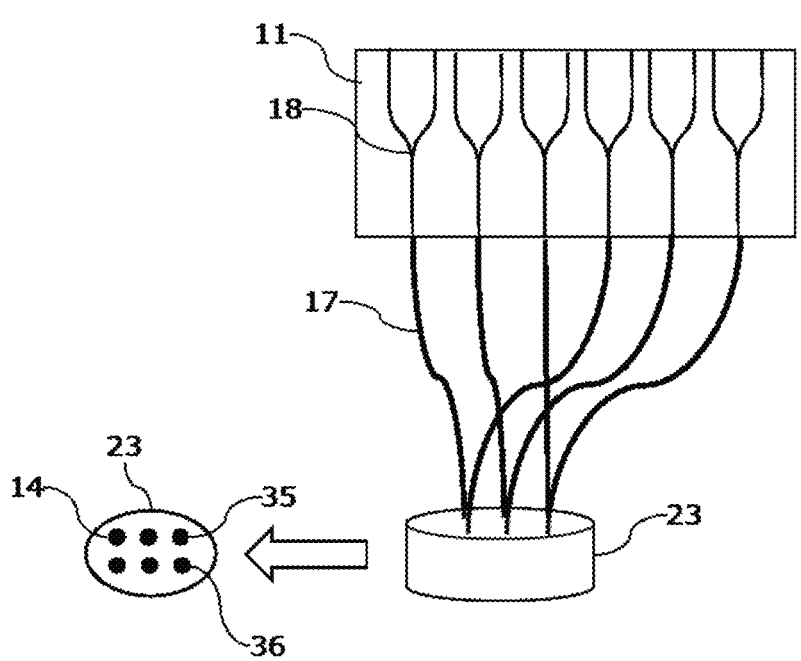
Fig. 3

INTEGRATED CHROMATIC CONFOCAL SENSOR

FIELD OF THE INVENTION

The invention relates to a multichannel confocal chromatic sensor.

The field of the invention is, but not limited to, 2D-3D inspection and metrology systems.

BACKGROUND

Chromatic confocal technique is a well-known technique for tridimensional (3D) surface mapping and thickness measurements, for semiconductor or other industrial applications.

The technique relies on the use of a chromatic lens with an enhanced chromatism, whose focal length depends strongly on the optical wavelength. Each wavelength of the light crossing such lens is focused at a different distance, or in a different focal plane.

The chromatic lens is embedded in a confocal set-up with source and detection apertures placed at confocal planes of the chromatic lens, so as to reject out-of-focus light. When a reflecting interface is placed in front of the chromatic lens, only the light with the wavelength whose focal plane corresponds to the position of the interface is transmitted by the detection aperture.

Detection is made by a spectrometer, which comprises usually a dispersing element and a sensor (CCD or CMOS) to acquire the intensity spectrum of the light. The height (or distance) of the interface relative to the chromatic lens is obtained by analyzing the intensity spectrum of the detected light.

Such set-up allows measuring distances on a single point at the time. So inspecting large surfaces may be very time-consuming.

Acquisition speed can be improved by providing several measurement channels in parallel.

For that, two kind of architectures are known, which are for instance described in the document FR 2 950 441.

It is for instance known to use a bulk beam splitter cube which is common to all the measurement channels. In that case, the light issued from the source apertures crosses the beam splitter and the chromatic lens, and the light reflected by the interfaces is directed by the same beam splitter towards the detection apertures.

This kind of arrangement allows providing a large number of channels, but it has the drawback that it is very difficult to adjust for matching optically the respective source and detection apertures of all the measurement channels. So usually this kind of architectures is implemented with an approximate confocal configuration, using for instance slits.

It is also known to use fiber couplers which direct the light from the source towards the chromatic lens, and the reflected light towards the detectors. Such configuration has the advantage that the source and detection apertures are the same (the end of a measurement fiber), and thus the optical alignment is very easy.

However, the fiber couplers have several drawbacks, notably:
- they are difficult to use with a very large number of channels;
- due do their principle of operation using coupling of modes between fiber cores, their coupling ratio is very dependent with the wavelength, which may introduce bias in the measurements.

It is an object of the invention to provide a chromatic confocal device allowing implementation of a large number of channels.

It is also an object of the invention to provide a chromatic confocal device allowing such implementation in a small volume.

It is also an object of the invention to provide a chromatic confocal device with a large number of channels which is easy to build and align.

It is also an object of the invention to provide a chromatic confocal device with optimal optical and metrological characteristics.

SUMMARY

Such objects are accomplished with a confocal chromatic device, comprising:
- at least one chromatic lens with an extended axial chromatism;
- at least one broadband light source;
- at least one optical detection means;
- characterized in that it comprises at least one measurement channel with a planar Y-junction made with a planar waveguide optics technology, and arranged for transferring light from said at least one light source towards said at least one chromatic lens and for transferring light reflected back through said at least one chromatic lens towards said at least one optical detection means.

The confocal chromatic device of the invention may comprise one or several measurement channels.

It may comprise any kind of chromatic lens or lens assembly having a suitable chromatic aberration over a field of view, such as for instance:
- a single lens or lens assembly shared between the optical measurement channels;
- a plurality of lenses or microlenses each used by only one or several optical measurement channels;
- holographic elements;
- diffractive lens or microlens elements.

It may notably comprise a chromatic lens with at least a lens made with a dispersive material, and any other lenses required for providing the necessary optical arrangement. Such chromatic lens may be designed according to well-known techniques so as to provide a strong chromatic aberration, allowing different optical wavelengths crossing the lens to be focused at different distances, or axial positions, over a lateral field of view.

The light source may comprise any kind of light source capable of emitting light at a plurality of wavelengths covering a spectral range for which the chromatism of the chromatic lens is efficiently usable. It may comprise for instance light-emitting diodes (LED), thermal light sources such as halogen lamps, or gas-discharge lamps. It may also comprise a tunable laser, a white laser or a supercontinuum photonic source. The light source may generate light with wavelengths within for instance a range of 400-700 nm (visible range) allowing inspection of surfaces and/or transparent layers in the visible range. Alternatively, the light source may generate light with wavelengths above 1 micron in the infrared range, allowing for instance inspections through layers of silicon or other materials transparent in the infrared.

The light source may comprise a single light source shared between all the optical measurement channels, or a plurality of light sources each shared between several optical measurement channels, or a light source per optical measurement channel.

The range of axial positions in which the optical wavelengths of the light source are focused by the chromatic lens define a chromatic measurement range.

A planar Y-junction as used in the invention may comprise a first waveguide which is enlarged progressively in a tapered zone (or a taper) ending in two branching waveguides. The tapered zone is preferably smooth enough to allow an adiabatic transition with a spread of the spatial modes of the guided light issued from the first waveguide, which are coupled in the branching waveguides.

Such arrangement has the advantage of being essentially achromatic over a broad spectral range. So, a fixed split ratio (for instance 50/50) may be obtained over such broad spectral range.

Of course the Y-junction is a reciprocal component, so a light issued from a branching waveguide is coupled in part (depending on the split ratio) to the first waveguide.

By contrast, the confocal chromatic devices of the prior art use fiber couplers, whose operating principle is based on the coupling of evanescent waves between cores of optical fibers brought to a close proximity. Such technology has the drawback that the coupling ratio is strongly dependent on the wavelength of the light. So, as a result, when used with broadband light sources, the fiber coupler introduce a strong chromatism which has to be taken into account and limit the detection efficiency.

According to some modes of realization, the device of the invention may comprise an achromatic planar Y-junction.

Such Y-junction may be achromatic at least over a spectral range of interest of the light source.

According to some modes of realization, the device of the invention may comprise a multimode planar Y-junction (and multimode waveguides).

According to some other modes of realization, the device of the invention may comprise a single mode planar Y-junction.

According to some modes of realization, the device of the invention may comprise an integrated optics component holding one or several planar Y-junctions.

The integrated optics component may be done with several techniques which allow doing optical waveguides, which are areas with a higher index of refraction embedded in a transparent substrate with a lower index of refraction.

For instance, the integrated optics component may be done using an ion-exchange process on a glass substrate. Such ion exchange occurs between a glass substrate and a molten salt bath when these are suitably brought into contact. This phenomenon locally increases the optical index of the glass by modifying its composition.

A thin metal layer is deposited on a glass substrate. Windows with a size of a few microns to a few tens of microns, with designs corresponding to waveguides, Y-junctions and other components, are opened in the metallic layer using a classical photolithography technique. A two-steps ion-exchange process is implemented to create the waveguides below to the glass surface. The first one consists in diffusing at high temperature ions such as silver ions into the glass wafer using a molten salt bath. Then, an electric field is applied for moving the ions and thus the waveguides deeper into the glass.

The integrated optics component may also be done using techniques involving deposition of layers of doped silica or other materials on wafers for constituting waveguides. The deposition steps usually involve CVD techniques.

The integrated optics component may also be done using direct inscription techniques. For instance, the waveguides may be done by modifying locally the index of refraction of a sol-gel substrate or a polymer resin with a UV laser beam, by photo-polymerization.

So, thanks to the use of the integrated optics component and the optical waveguide technology with the Y-junctions it is thus possible to make a device with a large number of measurement channels (such as a few hundred) which is very compact and easy to assemble.

In addition, the device will have superior performances, allowing better detection capabilities thanks to the achromatic behavior of the Y-junctions.

According to some modes of realization, the device of the invention may comprise an integrated optics component holding at least one measurement planar waveguide optically connected to a planar Y-junction, with an exit end optically facing a chromatic lens.

According to some modes of realization, the device of the invention may comprise at least one measurement optical fiber optically connected to a planar Y-junction, with an exit end optically facing a chromatic lens.

The device of the invention may also comprise a plurality of measurement optical fibers having exit ends spatially arranged in at least one row.

According to some modes of realization, the device of the invention may comprise an illumination optical fiber for transferring light between a light source and a planar Y-junction.

According to some modes of realization, the device of the invention may comprise a light source interfaced (or directly interfaced) to the integrated optics component.

According to some modes of realization, the device of the invention may comprise a detection optical fiber for transferring light from a Y-junction to optical detection means.

According to some modes of realization, the device of the invention may comprise optical detection means interfaced (or directly interfaced) to the integrated optics component.

According to some modes of realization, the device of the invention may comprise optical detection means with at least one of the following optical detectors: a spectral detector, a total intensity detector.

A total intensity detector (or intensity detector) may comprise any photodetector measuring an intensity of light, or a global intensity of light over a spectral range.

According to some modes of realization, such total intensity detector may comprise:

A separate or discrete intensity detector for each optical measurement channel, such as for instance a phototransistor, a photodiode or an avalanche photodiode; and/or An intensity detector shared between a pluralities of optical measurement channel. Such intensity detector may comprise for instance a photodiode array, or a line or matrix CCD or CMOS in which intensity measurements of different optical measurement channels are done on different pixels.

An intensity detector provides a global intensity information of the light reflected at a measurement point on an object within the chromatic measurement range. So it provides a 2D image information on the object.

The 2D measurements done with such intensity detector benefit from an extended depth of focus, because of the chromatic confocal set-up. The image which is obtained by these means is in focus or well-focused over the whole measurement range of the device, because it is done mostly using the wavelength focused on the surface of the object, whatever position that surface may have in the measurement range. And, thanks to the confocal arrangement, the light corresponding to the wavelengths which are out of focus is rejected.

By doing so, the available depth of focus for the imaging is determined by the extent of the chromatic aberration of the chromatic lens. It is thus much larger than the depth of focus which would be available with a classical achromatic lens, and which correspond to the depth of focus available for a single wavelength with the chromatic lens.

A spectral detector may comprise any detector capable of providing an information relative to an intensity of light in function of optical wavelengths (or an intensity spectrum), such as for instance:
- A spectrometer type device with a dispersing element such as a grating or a diffraction array and a sensor capable of collecting a light intensity for the different wavelengths, such as for instance a line CCD, CMOS or a photodiode array;
- A Fourier Transform spectrometer, built according to an interferometer scheme;
- A device with color filters in front of a line or matrix detector, allowing a detection which is selective in wavelength with different detector areas. Such device may comprise for instance sets of pixels having respectively red, green and blue filters. It may also have sets of pixels with color filters arranged in a Bayer filter configuration. Such device may then be arranged so that the light issued from an optical measurement channel illuminated a set of pixels with the relevant color filters.

A spectral detector may also comprise a detector shared between several optical measurement channels, such as line or matrix CCD or CMOS. In that case, intensity spectra of different optical measurement channels are collected on different areas or pixels of the detector using for instance a dispersing element or color filters.

A spectral detector allows obtaining an axial distance information, or a height information at a measurement point on an object within the chromatic measurement range. The axial distance information may be deduced for instance from the intensity spectrum by identifying the peak(s) in the spectrum or the wavelengths which are the most reflected, and which are representative of the location of the corresponding interfaces of an object in the measurement range. Of course, in presence of a transparent object with several detectable layers, several peaks representative of optical distances to several interfaces may be identified.

When using a detector with color filters, the axial distance information may be deduced for instance by comparing relative intensities measured by pixels with different color filters.

So, a spectral detector provides a 3D information which is the usual purpose of the chromatic confocal sensors.

The invention thus allows doing a sensor with 2D and/or 3D inspection capabilities.

According to some modes of realization, the device of the invention may comprise optical detection means allowing operation simultaneously as a spectral detector and a total intensity detector.

For instance, the optical detection means may comprise a detector with pixels in lines or matrix, at least some of which having color filters, allowing:
- measurement of axial distance information by comparing relative intensities measured by pixels with different color filters, and
- measurement of total intensity. Such measurement of total intensity may be for instance done by combining (or summing) intensities measured by pixels with different color filters. It may also be done by using a detector having pixels with color filters and pixels without color filters on the same pixel matrix, and allowing for instance measuring for a measurement channel intensities with four pixels having respectively red, green, blue filters, and no filter.

The device of the invention may notably comprise:
- Only measurement channels with a total intensity detector;
- Only measurement channels with a spectral detector;
- Measurement channels with a spectral detector, and measurement channels with a total intensity detector;
- Measurement channels with a spectral detector and a total intensity detector on a same channel;

2D total intensity measurement can be done much faster than 3D axial distance measurements, because their only limitation in terms of acquisition rate relate to the integration time or bandwidth of the detector. In the other hand, 3D axial measurement rates are limited at least by the integration time and readout time of spectrometer sensors. As consequence, 2D measurement may be done at acquisitions rates 3 times or even much faster than 3D measurements. For instance 2D measurement may be done at acquisition rates of several tens of kilohertz (for instance 50 KHz to 100 KHz), whereas 3D measurements may be done only at acquisition rates from a few kilohertz to a few tens of kilohertz.

So, the device of the invention is particularly well adapted for high speed inspection, because it allows for instance:
- fast 2D inspection with an extended depth of focus, allowing for instance inspection of the surface of an object with extended tridimensional structures (such as bumps, pillars, nails, . . . on a wafer) with an optimal lateral resolution at any measurement points without refocusing; and/or
- fast 2D inspection of the surface of a structured object, and on-the-fly 3D measurement at selected points of interest; and/or
- 3D measurement.

According to some modes of realization, the device of the invention may comprise a spectral detector and a total intensity detector optically connected to a same planar Y-junction.

According to some modes of realization, the device of the invention may comprise a secondary planar Y-junction for directing the light issued from a planar Y-junction towards a spectral detector and a total intensity detector.

According to some modes of realization, the device of the invention may comprise a spectral detector of the Fourier spectrometer type made with:
- a portion of optical waveguide terminated by an end mirror to generate a standing wave; or
- a planar Y-junction and a loop of optical waveguide arranged to split an incident wave into two contra-propagative waves.

According to some modes of realization, the device of the invention may comprise an integrated optics component with planar waveguides crossing planar waveguides of other measurement channels so as to group at least planar waveguides optically connected to light source.

DESCRIPTION OF THE DRAWINGS

The methods according to embodiments of the present invention may be better understood with reference to the drawings, which are given for illustrative purposes only and are not meant to be limiting. Other aspects, goals and advantages of the invention shall be apparent from the descriptions given hereunder.

FIG. 1 illustrates a mode of realization of the device of the invention;

FIG. 2 illustrates a y-coupler;

FIG. 3 illustrates a mode of realization with measurement optical fibers;

DETAILED DESCRIPTION

Figure 4:
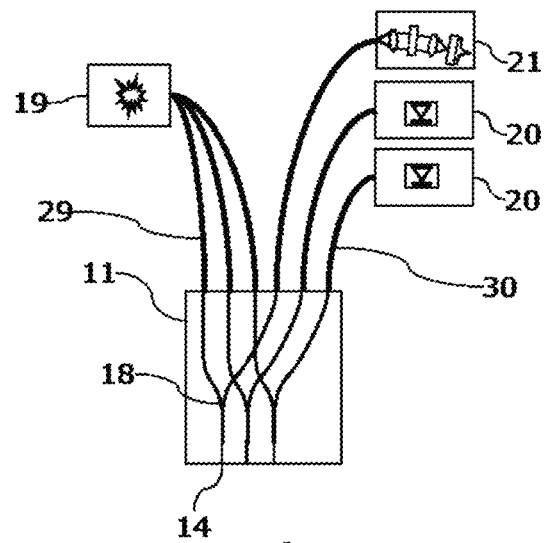
FIG. 4 illustrates a mode of realization with crossings of planar waveguides.

It is well understood that the embodiments described hereinafter are in no way limitative. Variants of the invention can in particular be envisaged comprising only a selection of the features described below in isolation from the other described features, if this selection of features is sufficient to confer a technical advantage or to differentiate the invention with respect to the state of the prior art. This selection comprises at least one preferred functional feature without structural details, or with only one part of the structural details if this part alone is sufficient to confer a technical advantage or to differentiate the invention with respect to the state of the prior art.

In particular, all the described variants and embodiments can be combined if there is no objection to this combination from a technical point of view.

In the figures, the elements common to several figures retain the same references.

With reference to FIG. 1 and FIG. 2, we will describe a confocal chromatic device of the invention.

The chromatic device of the invention comprises a chromatic lens 13 and an integrated optics component 11 with optical waveguides 25 and Y-junctions 18 of a plurality of optical measurement channels 24.

The chromatic lens 13 (or lens arrangement 13) is designed according to well-known techniques so as to provide a strong chromatic aberration, allowing different optical wavelengths crossing the lens to be focused at different axial distances (that is distances along the optical axis of the lens, or along the Z axis as shown in FIG. 1).

In the mode of realization of FIG. 1, the chromatic lens 13 is represented by a doublet with an extended lateral field, allowing measurements with all the measurement channels 24. It comprises a first lens set which is achromatic and a second lens set facing the object 10 under measurement which exhibit a strong chromatic aberration.

The optical measurement channels 24 comprise a collection aperture 14 from which an illumination light is issued, and which collects measurement light reflected back by the object 10 under measurement.

The light issued from a collection aperture 14 is focused by the chromatic lens 13 on a measurement point 15, or more precisely along a measurement line 15 in the Z direction depending on the wavelengths. So the spatial repartition of the collection apertures along the X-Y directions (or in an X-Y plane) determines a spatial repartition of measurement point 15 in the X-Y plane.

The optical measurement channels 24 are illuminated by a broadband light source 19. In the modes of realization presented, that light source 19 may comprise a thermal source (halogen for instance) or a LED source generating light with wavelengths within for instance a range of 400-700 nm (visible range).

The range of axial positions along the Z axis in which the optical wavelengths of the light source 19 (issuing from the collection aperture 14) are focused by the chromatic lens 13 define a chromatic measurement range.

When an interface of an object 10 is present in the chromatic measurement range, the wavelengths focused on that interface are reflected within the collection apertures 14. The other wavelengths are rejected thanks to the confocal configuration of the set-up, with illumination and collection apertures (both made by the collection aperture 14) which are conjugate of the measurement points 15 for the chromatic lens 13 only at the wavelengths focused on the interface of the object 10.

The measurement channels 24 comprise a Y-junction 18 made with a planar waveguide technology. That Y-junction 18 conveys the light from the light source 19 towards the collection aperture 14, and conveys the measurement light collected by the collection aperture 14 towards detectors 20, 21.

FIG. 2 shows an example of such Y-junction. It comprises a first waveguide 25 which is enlarged progressively in a tapered zone 26 ending in two branching waveguides 27. As previously explained, the tapered zone 26 allows a spread of the spatial modes 28 of the guided light issued from the first waveguide 25, which are coupled in turn in the branching waveguides 27.

In the mode of realization of FIG. 1, the Y-junction 18 of all the measurement channels 24 are done on a same integrated optics component 11.

The device further comprises a set of illumination optical fibers 29 to bring the light from the light source 19 to the Y-junctions 18 on the integrated optics component 11.

It also comprises a set of detection fibers 30 to bring the measurement light issued from the collection apertures 14, through the respective Y-junctions, to detection means 20, 21.

The illumination fibers 29 and the detection fibers 30 are interfaced with optical waveguides 25 of the integrated optics component 11 on an edge of such component 11 using known coupling techniques.

Such coupling techniques may comprise for instance V-grooves for maintaining the fibers, and/or microlenses and/or tapers in waveguides for the optical coupling. They have the advantage of allowing coupling of even hundreds of fibers to optical waveguides with well automated methods and low coupling power losses.

For instance, the optical fibers are arranged in a flat bundle with an accurate spacing between the fiber cores. Their ends are held in silicon V-grooves (for instance with glue) so as to face the respective optical waveguides 25 of the measurement channels 24, which are etched in the optical integrated component 11 with a spacing matching the spacing of the fibers.

In the mode of realization of FIG. 1, the collection apertures 14 are done directly by end of optical waveguides 25 at an edge of the integrated optics component 11.

The integrated optics component 11 may be done with any of the methods described previously. In preferred embodiments however, it is done using an ion-exchange process on a glass substrate or a direct inscription technique, which have the advantage of allowing low-cost production of small batches of components.

The optical waveguides and Y-junctions may be single mode. However, in preferred modes of realization, multimode waveguides are used, with lateral dimension in the order of 50 µm to 100 µm. Such multimode waveguides allow efficient coupling of optical power and easy interfacing with multimode optical fibers with core of similar dimension.

As explained previously, the light reflected at the measurement points 15 by an object 10 positioned in the measurement range is coupled back in the collection apertures 14. Thanks to the confocal arrangement of the set-up, only the light actually focused on an interface of the object 10 is coupled back in the collection apertures 14, and the light reflected by the object 10 out-of-focus is not coupled back.

In addition, thanks to the chromatic dispersion of the chromatic lens 13:
  The light focused on an interface (or a surface) of the object 10 correspond essentially to a single wavelength or group of wavelength for which the focal length of the chromatic lens 13 corresponds to the axial optical distance to that interface along the optical axis of the lens (corresponding to the Z axis). So by analyzing the intensity spectrum of the reflected light, the axial distance to the interfaces may be measured. That measurement mode, which corresponds to a classical use of the chromatic confocal technique, may be called profilometry mode or 3D detection mode;
  The light collected after reflection on an interface (or a surface) of an object 10 located anywhere within the measurement range does not include any significant defocused light (thanks to the confocal arrangement) but only light focuses on that interface or surface. So it provides an intensity information with a lateral resolution in the object plane (X-Y) corresponding to the spot size at focus. And such lateral resolution is achieved for interfaces or surfaces located within the whole measuring range. So, by analyzing the total intensity of the reflected light, the set-up allows imaging interfaces or surfaces of the object 10 with a high lateral resolution over an extended depth of focus, which is superior to the depth of focus achieved for any single wavelength, or which would be achieved by a classical achromatic optical set-up. This measurement mode has thus the advantage of allowing intensity imaging of surfaces of structures on the object 10 with a significant height (as shown in FIG. 1) with an optimal lateral resolution in a 2D (bidimensional) detection mode.

The light coupled back in the collection apertures is transferred through the Y-junctions to detection means 20, 21, which may comprise:
  Intensity detectors 20 allowing measuring a total intensity of the collected light; and/or
  Spectral detectors 21 allowing measuring a spectral information on the collected light.

According to some modes of realization, the device of the invention comprises only optical measurement channels 24 with an intensity detector 20 for measuring a total intensity of the collected light. In that case the device of the invention is devoted to fast 2D inspection (intensity imaging) with an extended depth of focus.

According to some modes of realization, the device of the invention comprises only optical measurement channels 24 with a spectral detector 21 for measuring a spectral information on the collected light, and obtaining an axial distance information. In that case the device of the invention is devoted to 3D detection mode (profilometry).

According to some modes of realization, the device of the invention comprises optical measurement channels 24 with (or coupled with) an intensity detector 20 and/or a spectral detector 21 for respectively acquiring data in 2D detection mode (intensity imaging) and/or 3D measurement mode (profilometry).

In all cases, the light coupled back in the collection apertures 14 is transferred to these intensity detectors 20 and/or spectral detectors 21 by the Y-junctions splitter 18.

Several arrangements of intensity detectors 20 and spectral detectors 21 within or in relation with the optical measurement channels 24 are possible.

Figure 5:
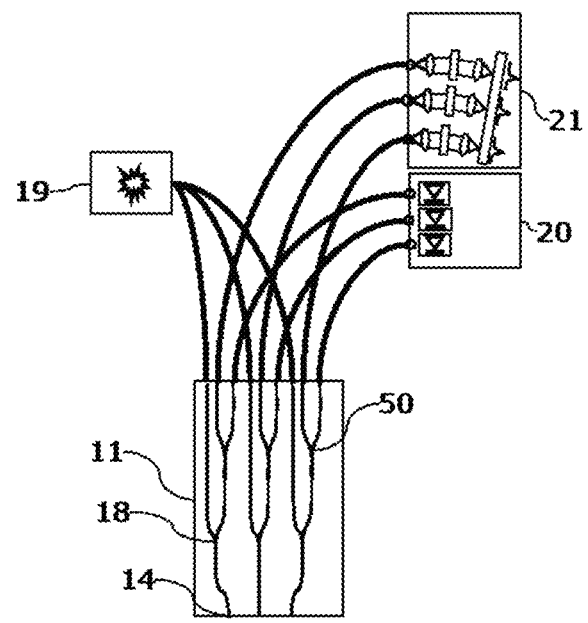
FIG. 5 illustrates a mode of realization with secondary Y-junctions.

The device of the invention may notably comprise:
  Optical measurement channels 24 which comprise only an intensity detector 20 or a spectral detector 21, as illustrated for instance on FIG. 1. In that case, these optical measurement channels 24 are dedicated to an intensity (2D) measurement or an axial distance (3D) measurement at the corresponding measurement point 15;
  Optical measurement channels 24 which comprise an intensity detector 20 and a spectral detector 21. In that case, these optical measurement channels 24 further comprise a secondary Y-junction as illustrated in FIG. 5, for directing the light coupled back in the collection apertures 14 simultaneously towards the intensity detector 20 and the spectral detector 21. In that case, these optical measurement channels 24 allow doing intensity measurements (2D) and axial distance measurements (3D) at the corresponding measurement point 15;

The spectral detectors 21 as illustrated notably in the mode of realization of FIG. 1 comprise:
  An entrance pupil, corresponding for instance to an end of an optical fiber, and a first lens for collimating the incoming light issued from the entrance pupil;
  A dispersing element such as a diffraction array or a grating for dispersing angularly the different wavelengths of the incoming light;
  A second lens and a linear detector such as a line CDD for re-imaging the dispersed light so that different wavelengths are focused on different pixels of the sensor. The intensity spectrum of the light is obtained by collecting the information on the pixels of the sensor. An interface of the object 10 present in the measurement range gives rise to a peak in the intensity spectrum around the wavelength focused at the corresponding axial position. So the intensity spectrum is analyzed to obtain an axial distance information, or the position of the interfaces or the surface of the object 10 within the measurement range.

The spectral detectors 21 of the different measurement channels 24 may be completely distinct, or, as illustrated in FIG. 5, they may share some elements such as the detector. For instance, several spectral detectors 21 may share a same line or matrix sensor, the information of each spectral detectors 21 being collected on a separate set of pixels of the shared detector. In the same way, several spectral detectors 21 may share a same dispersing element.

The intensity detectors 20 comprise point detectors such as photodiodes which measure the whole intensity of the light over the full spectrum.

The intensity detectors 20 of the different measurement channels 24 may be distinct (using for instance individual photodiodes), or, as illustrated in FIG. 5, they may share some elements such as the detector. For instance, several intensity detectors 20 may share a same photodiode array, or a same line or matrix sensor (CCD or CMOS), the information of each intensity detectors 20 being collected on a separate pixel, set of pixel or photodiode.

The device of the invention further comprises a computer or a microcontroller 22 for control and data processing.

For allowing inspection of an object 10 such as a wafer, the device of the invention may further comprises a holder for holding the object 10 (for instance a wafer chuck) and a mechanical displacement stage 16 for moving relatively the integrated optics component 11 with the chromatic lens 13 and the object 10. In the mode of realization presented, the mechanical displacement stage 16 may comprise translation plates for linear displacements along the X, Y, and Z axis, and a rotation stage for rotating the object 10 in the X-Y plane.

FIG. 3 illustrates mode of realization in which the device comprises a set of measurement fibers 17 for conveying the light between the optical waveguides 25 of the integrated optics component 11 and the chromatic lens 13.

These measurement fibers 17 are interfaced on a first end with the optical waveguides 25 of the integrated optics component 11 on an edge of such component 11 using known technologies.

As previously explained, such coupling technologies may comprise for instance V-grooves for maintaining the fibers, and/or microlenses and/or tapers in waveguides for the coupling.

The measurement fibers have a second end which constitutes the respective collection apertures 14 of the measurement channels 24.

Such configuration has the advantage of allowing spatial arrangement of the collection apertures 14 which are different from the spatial arrangement of the end of the optical waveguides 25 on the integrated optics component 11.

An example of measurement configuration is illustrated on FIG. 3, which is suitable for instance for high-speed inspection of a surface of an object 10 such as a wafer with structures such as bumps or micro-bumps.

According to that example, the measurement fibers 17 of the respective optical measurement channels 24 are arranged so that their end forming the collection apertures 14 are positioned in two parallel rows 35, 36 positioned in a mounting piece 23 (for instance with grooved elements for accurately positioning the fiber ends).

A first row 35 comprises measurement fibers 17 of measurement channels 24 connected to intensity detectors 20.

A second row 36 comprises measurement fibers 17 of measurement channels 24 connected to spectral detectors 21.

The first row 35 and the second row 36 may have a same number of collection apertures 14 as illustrated in FIG. 3, or a different number, possibly with a different spacing.

The second row 36 may even have a single collection apertures 14 connected to a single spectral detector 21.

That arrangement allows for instance acquiring intensity information prior to axial distance information in a same scan.

It allows for instance implementing a method for inspecting a surface of an object in 2D and 3D modes.

Such method comprises steps of:
Acquiring an intensity information with several measurement channels 24 on several measurement points 15 at the surface of the object 10, for instance using the measurement channels of the first row 35;
Locating points of interests for axial distances measurements using said intensity information and possibly intensity information and/or axial distance information acquired during preceding steps;
Positioning collection apertures 14 (for instance of the second row 36) of at least one measurement channel 24 with a spectral detector 21 over a point of interest;
Acquiring at least one axial distance information;
repeating the process over the surface of the object 10 and computing the results.

The computation may comprise for instance at least one of the following: Building a height map, building an intensity map, locating structures in the X-Y plane, comparing height or in-plane dimensions of the structures with expected values, issuing pass/fail data.

Of course, other repartitions of the collection apertures 14 are possible.

For instance, the collection apertures 14 done with optical waveguides 25 (as illustrated in FIG. 1) or measurement fibers 17 (as illustrated in FIG. 3) may be arranged in one row. And these collection apertures 14 may optically connected to:
Only intensity detectors 20;
Only spectral detectors 21;
Intensity detectors 20, except for one or several collection apertures 14 located at the center of the row which are optically connected to spectral detectors 21;
. . . or any other configuration.

FIG. 4 illustrated a mode of realization of the integrated optics component 11 in which the branching waveguides 27 cross each other so as to allow respectively grouping the illumination optical fibers 29 and the detection optical fibers 30 on a side of the integrated optics component 11, instead of having them interleaved as shown on FIG. 1 for instance.

Crossing of waveguides 27 (which are on a same layer) is possible with reasonably low amounts of crosstalk, provided that the crossing angle between the waveguides is higher than a given value, such as for instance 10 degrees, or better 30 degrees.

Such configuration of the integrated optics component 11 may of course be used with the other modes of realization presented.

FIG. 5 illustrates a mode of realization in which the measurement channels 24 comprise a secondary planar Y-junction 50 for directing the measurement light issued from the main planar Y-junction 18 simultaneously towards a spectral detector 21 and a total intensity detector 20.

The main planar Y-junctions 18 and the secondary Y-junctions 50 are preferably done on the same integrated optics component 11 for a better integration.

As previously explained, such configuration allows doing spectral measurements and total intensity measurements with the same measurement channels 24.

Of course, it is possible to have only a part (such as only one or some) of the measurement channels 24 having such secondary planar Y-junction 50. In that case, the other measurement channels are optically connected only to a spectral detector 21 or a total intensity detector 20, as illustrated for instance in FIG. 1.

Figure 6:
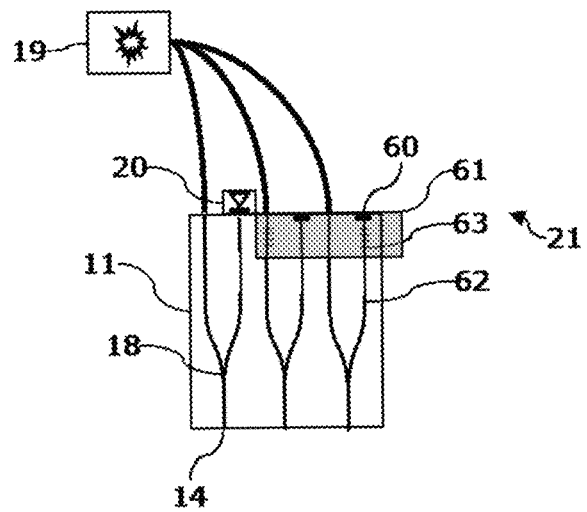
FIG. 6 illustrates a mode of realization with a first Fourier spectrometer.
Figure 7:
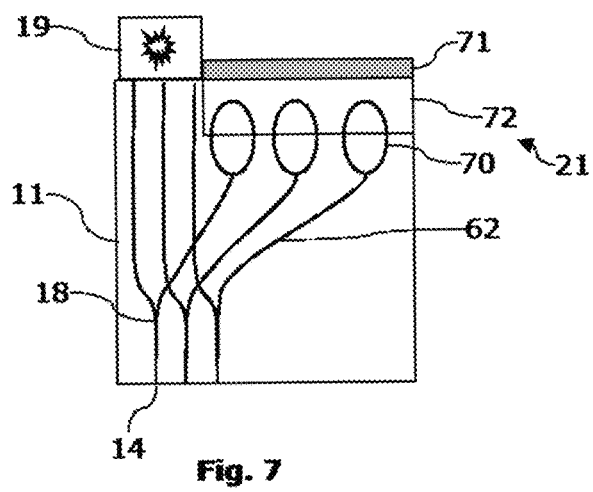
FIG. 7 illustrates a mode of realization with a second Fourier spectrometer.

FIG. 6 and FIG. 7 illustrate modes of realization of the invention which comprise spectral detectors 21 done with techniques which can be implemented on an integrated optics component 11.

These spectral detectors 21, which will be described in details later, are based on Fourier transform spectrometer configurations which can be done with a planar waveguide technology. Such Fourier transform spectrometers provide time-domain interferograms of the measurement signal, from which an intensity spectrum is deduced by applying a Fourier transform.

In that case, the device of the invention can be done in a very compact shape with an integrated optics component 11 holding most of the features.

Of course, in the modes of realization of FIG. 6 and FIG. 7, the device of the invention may also comprise total intensity detectors 20.

With reference to FIG. 6, we will now describe a first mode of realization of Fourier transform spectrometer.

Such Fourier transform spectrometer is for instance described in the document WO 2006/064134, and in the article: Etienne le Coarer, Sylvain Blaize, Pierre Benech, Ilan Stefanon, Alain Morand, Gilles Lérondel, Grégory Leblond, Pierre Kern, Jean Marc Fedeli, Pascal Royer, <<Wavelength-scale stationary-wave integrated Fourier transform spectrometry>>, Nature Photonics 1, 473-478 (2007). So, for conciseness, only the essential elements are described here.

The Fourier transform spectrometer comprises a measurement waveguide 62 which receives the measurement light issued from a Y-junction 18.

The measurement waveguide 62 is terminated by a reflecting element 60 (such as for instance a metallic or dielectric coating on the side of the integrated optics component 11).

A matrix detector 61 (such as an array CCD or CMOS) is placed above the measurement waveguide 62, preferably covering several of such measurement waveguides 62.

The measurement light incident on the measurement waveguide 62, corresponding to an incident wave, is reflected back by the reflecting element 60, so as to form a contra-propagative reflected wave.

A set of nanowires 63 (such as gold nanowires) are periodically deposited on the surface of the waveguide 62. They behave as diffusing centers 63 for the evanescent waves at the boundary of the waveguide 62.

So, the incident and reflected waves are spatially sampled by these diffusing centers 63, generating diffused light for both waves which interfere on the detector 61.

The interference of the incident and reflected waves give rise to an interferogram (or time domain autocorrelation) of the measurement light with the zero optical path difference on the reflecting element 60.

The interferogram as spatially sampled by the diffusing centers 63 is recorded by the matrix detector 61. The sampling resolution correspond to the size of the diffusing centers 63, while the sampling period correspond to the interval between consecutive diffusing centers 63.

Because of the pixel size of the usual matrix detectors 61, the sampling period along one waveguide 62 is not small enough to satisfy the Shannon sampling theorem. To solve that issue, a measurement light may be directed to several parallel measurement waveguides 62 by means of Y-junctions. These parallel measurement waveguides 62 comprise diffusing centers 63 shifted in position (for instance by depositing gold nanowires over the parallel measurement waveguides 62 forming with these measurement waveguides 62 an angle different from a right angle), so that by interleaving the measurements obtained on all the measurement waveguides 62 a complete interferogram may be reconstructed.

With reference to FIG. 7, we will now describe a second mode of realization of Fourier transform spectrometer.

Such Fourier transform spectrometer is for instance described in the document WO 2007/017588. So, for conciseness, only the essential elements are described here.

The Fourier transform spectrometer comprises a measurement waveguide 62 which receives the measurement light issued from a Y-junction 18. The measurement waveguide ends on a loop waveguide 70 formed by a branching Y-junction with two exits branches forming a same circular waveguide.

The measurement light incident on the measurement waveguide 62, corresponding to an incident wave, is split by the branching Y-junction in two waves which propagate within the loop 70 in opposite directions.

The spectrometer further comprises a planar waveguide diverging area 72 arranged so that the waves within the loop 70 may "leak" within that diverging area 72 and propagate through it while being confined in a waveguide layer.

The diverging area is terminated by a line detector 71 (CCD or CMOS) located on the edge of the integrated optics element. The two contra-propagative waves leaking from the loop 70 propagate through the diverging area 72 and interfere on the line detector 71. The interference of these two contra-propagative waves give rise to an interferogram (or time domain autocorrelation) of the measurement light.

Thanks to the propagation through the diverging area 72, the interferogram as recorded by the line detector 71 is magnified by a magnification factor corresponding to R(x)/r, where r is the radius of curvature of the loop 70 and R(x) is the radial distance from the center of curvature of the loop 70 to the location at position x on the detector 71. So, by adjusting the width of the diverging area 72, it is possible to have an interferogram at the detector which is large enough so that the pixel size of the line detector 71 is able to satisfy the Shannon sampling theorem.

According to some variants of all the modes of realization, the device of the invention may comprise light sources 19 which are interfaced to the optical waveguides 25, 27 of the integrated optics component 11 without illumination optical fibers 29, as illustrated in FIG. 7. Such light sources 19 may comprise for instance LEDs interfaced to the waveguides 25, 27 on an edge of the integrated optics component, directly or through a taper or a micro-lens.

According to some variants of all the modes of realization, the device of the invention may comprise total intensity detectors 20 which are interfaced to the optical waveguides 25, 27 of the integrated optics component 11 without detection optical fibers 30, as illustrated in FIG. 6. Such total intensity detectors 20 may comprise for instance photodiodes or line CCD or CMOS interfaced to the waveguides 25, 27 on an edge of the integrated optics component, directly or through a taper or a micro-lens.

According to some variants of all the modes of realization, the device of the invention may comprise spectral detectors 21 which are interfaced to the optical waveguides 25, 27 of the integrated optics component 11 without detection optical fibers 30. For instance:
  a spectral detector 21 of a spectrometer type device with a dispersing element may be positioned so as to have the end of one or several optical waveguides 25, 27 on an edge of the integrated optics component 11 positioned in or so as to constitute its entrance slit;
  a spectral detector 21 with color filters in front of a line or matrix detector (possibly operating also as a total intensity detectors 20) may comprise for instance groups of pixels arranged so as to be illuminated by waveguides 25, 27 on an edge of the integrated optics component, directly or through a taper or a micro-lens.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A confocal chromatic device, comprising:
   a chromatic lens assembly with an extended axial chromatism;
   at least one broadband light source;
   at least one optical detection means;
   a plurality of measurement channels each comprising a planar Y-junction made with a planar waveguide optics technology, and arranged for transferring illumination light from said at least one light source towards said chromatic lens assembly and an object, and for transferring measurement light reflected back by said object on a measurement point through said chromatic lens assembly towards said at least one optical detection means,
   said planar Y-junction comprising a first waveguide which is enlarged progressively in a tapered zone ending in two branching waveguides, said planar Y-junction being achromatic at least over a spectral range of interest of said light source; and
   an integrated optics component holding the planar Y-junctions and the waveguides of said measurement channels, wherein said measurement channels each comprise a collection aperture from which said illumination light is issued and which collects the measurement light in a confocal configuration with said collection aperture being conjugate of the measurement point for the chromatic lens assembly, said collection apertures being directly at ends of the waveguides at an edge of the integrated optics component, and facing the chromatic lens assembly so that the spatial repartition of said collection apertures determines a spatial repartition of the measurement points on the object.

2. The device of claim 1, wherein said planar Y-junction is a multimode planar Y-junction.

3. The device of claim 1, further comprising an illumination optical fiber configured for transferring light between said light source and said planar Y-junction.

4. The device of claim 1, wherein said light source is interfaced to said integrated optics component.

5. The device of claim 1, further comprising a detection optical fiber configured for transferring light from said planar Y-junction to said at least one optical detection means.

6. The device of claim 1, wherein said at least one optical detection means is interfaced to said integrated optics component.

7. The device of claim 1, wherein said at least one optical detection means includes at least one of the following optical detectors: a spectral detector and a total intensity detector.

8. The device of claim 7, further comprising a spectral detector and a total intensity detector optically connected to said planar Y-junction.

9. The device of claim 8, further comprising a secondary planar Y-junction configured for directing the light issued from said planar Y-junction towards said spectral detector and said total intensity detector.

10. The device of claim 1, wherein said at least one detection means comprise a spectral detector of the Fourier spectrometer type made with:
    a portion of optical waveguide terminated by an end mirror to generate a standing wave; or
    said planar Y-junction and a loop of optical waveguide arranged to split an incident wave into two contra-propagative waves.

11. The device of claim 1, further comprising an integrated optics component with planar waveguides crossing planar waveguides of other measurement channels so as to group said planar waveguides optically connected to said light source.

12. The device of claim 1, wherein said at least one optical detection means includes a total intensity detector configured for measuring the whole intensity of light over the full spectrum.

* * * * *